(12) United States Patent
Jang et al.

(10) Patent No.: US 12,121,337 B2
(45) Date of Patent: Oct. 22, 2024

(54) APPARATUS AND METHOD FOR ESTIMATING BIO-INFORMATION

(71) Applicants: SAMSUNG ELECTRONICS CO., LTD., Suwon-si (KR); University of Maryland, College Park, College Park, MD (US)

(72) Inventors: Dae Geun Jang, Yongin-si (KR); Sungtae Shin, Busan (KR); Jin-Oh Hahn, Potomac, MD (US); Ui Kun Kwon, Hwaseong-si (KR); Youn Ho Kim, Hwaseong-si (KR); Peyman Yousefian, Quincy, MA (US)

(73) Assignees: SAMSUNG ELECTRONICS CO., LTD., Suwon-si (KR); University of Maryland, College Park, College Park, MD (US)

( * ) Notice: Subject to any disclaimer, the term of this patent is extended or adjusted under 35 U.S.C. 154(b) by 672 days.

(21) Appl. No.: 17/227,476

(22) Filed: Apr. 12, 2021

(65) Prior Publication Data

US 2021/0330206 A1 Oct. 28, 2021

Related U.S. Application Data

(60) Provisional application No. 63/013,760, filed on Apr. 22, 2020.

(30) Foreign Application Priority Data

Mar. 11, 2021 (KR) .................. 10-2021-0031885

(51) Int. Cl.
*A61B 5/024* (2006.01)
*A61B 5/0205* (2006.01)
(Continued)

(52) U.S. Cl.
CPC ........ *A61B 5/02416* (2013.01); *A61B 5/0205* (2013.01); *A61B 5/02116* (2013.01); *A61B 5/1102* (2013.01); *G06N 7/01* (2023.01)

(58) Field of Classification Search
CPC .............. A61B 5/02416; A61B 5/0205; A61B 5/02116; A61B 5/1102; A61B 5/349; G06N 7/01
See application file for complete search history.

(56) References Cited

U.S. PATENT DOCUMENTS 8,870,780 B2   10/2014   Inan et al.
9,314,181 B2   4/2016    Brockway et al.
(Continued)

FOREIGN PATENT DOCUMENTS

KR   1020130129319 A   11/2013
KR     101509959 B1    4/2015

OTHER PUBLICATIONS

Lu, H. et al., "A Novel Deep Learning based Neural Network for Heartbeat Detection in Ballistocardiograph", Proc. of Ann. Int. IEEE EMBS Conf., pp. 2563-2566, 2018.
(Continued)

*Primary Examiner* — Eric F Winakur
*Assistant Examiner* — Abid A Mustansir
(74) *Attorney, Agent, or Firm* — Sughrue Mion, PLLC

(57) ABSTRACT

An apparatus for estimating bio-information of a user may include a first sensor configured to measure a first signal from the user; a second sensor configured to measure a second signal from the user; and a processor configured to obtain a first characteristic point from the first signal; obtain a second characteristic point from the second signal based on the first characteristic point and a pre-defined probability distribution function; and estimate the bio-information of the user based on the second characteristic point.

17 Claims, 16 Drawing Sheets

(51) Int. Cl.
    *A61B 5/021*     (2006.01)
    *A61B 5/11*     (2006.01)
    *G06N 7/01*     (2023.01)

(56) References Cited

U.S. PATENT DOCUMENTS

| | | | |
|---|---|---|---|
| 2011/0251502 A1* | 10/2011 | Friedrich | A61B 5/1102 600/500 |
| 2012/0123279 A1 | 5/2012 | Brueser et al. | |
| 2013/0158415 A1 | 6/2013 | Kim et al. | |
| 2015/0018637 A1* | 1/2015 | Chen | A61B 5/0295 600/301 |
| 2015/0126876 A1 | 5/2015 | Lee et al. | |
| 2018/0289288 A1 | 10/2018 | Kim et al. | |
| 2019/0046069 A1 | 2/2019 | Centen et al. | |
| 2019/0231271 A1 | 8/2019 | Borkholder et al. | |
| 2019/0274552 A1 | 9/2019 | Jang et al. | |
| 2020/0196959 A1 | 6/2020 | Jang et al. | |

OTHER PUBLICATIONS

Sprager, S., et al., "Optimization of Heartbeat Detection in Fiber-Optic Unobtrusive Measurements by Using Maximum A Posteriori Probability Estimation", IEEE Journal of Biomedical and Health Informatics, vol. 18, No. 4, Jul. 2014, pp. 1161-1168.

Yousefian, P., et al., "The Potential of Wearable Limb Ballistocardiogram in Blood Pressure Monitoring via Pulse Transit Time", Scientific Reports, Jul. 23, 2019, pp. 1-11.

Shin, J. H., et al., Automatic Ballistocardiogram (BCG) Beat Detection Using a Template Matching Approach, 30th Annual International IEEE EMBS Conference, Aug. 20-24, 2008, pp. 1144-1146.

Yao, Y., et al., "Unobtrusive Estimation of Cardiovascular Parameters with Limb Ballistocardiography", Sensors, vol. 19, No. 2922, Jul. 1, 2019, pp. 1-18.

* cited by examiner

APPARATUS AND METHOD FOR ESTIMATING BIO-INFORMATION

CROSS-REFERENCE TO RELATED APPLICATION(S)

This application is based on and claims priority under 35 U.S.C. § 119 to Korean Patent Application No. 10-2021-0031885, filed on Mar. 11, 2021, in the Korean Intellectual Property Office, and U.S. Provisional Application No. 63/013,760, filed on Apr. 22, 2020, in the U.S. Patent & Trademark Office, the disclosures of which are incorporated by reference herein in their entireties.

BACKGROUND

1. Field

The following description relates to an apparatus and method for estimating bio-information, and, more particularly, to technology for obtaining characteristic points for estimating bio-information from a ballistocardiogram (BCG) signal.

2. Description of Related Art

As our society is rapidly aging, healthcare technology has attracted much attention due to social problems such as the increase in medical expenses. Accordingly, not only medical devices for use in hospitals or medical examination institutions, but small medical devices that individuals can carry are also being developed. Furthermore, such small medical devices are worn by users in the form of wearable devices capable of directly measuring cardiovascular health status such as blood pressure, and the like, thereby enabling users to directly measure and manage cardiovascular health status. Therefore, in order to provide devices in a compact size with improved accuracy in estimating bio-information, a lot of research has been conducted recently on methods of estimating bio-information by analyzing bio-signals.

SUMMARY

Provided is an apparatus and method for detecting characteristic points for estimating bio-information from a ballistocardiogram (BCG) signal based on a probability distribution function, and for estimating bio-information based on the detected characteristic points.

According to an aspect of the disclosure, an apparatus for estimating bio-information of a user may include a first sensor configured to measure a first signal from the user; a second sensor configured to measure a second signal from the user; and a processor configured to obtain a first characteristic point from the first signal; obtain a second characteristic point from the second signal based on the first characteristic point and a pre-defined probability distribution function; and estimate the bio-information of the user based on the second characteristic point.

The first signal may include at least one of an electrocardiography (ECG) signal, a photoplethysmogram (PPG) signal, an electromyography (EMG) signal, an impedance plethysmogram (IPG) signal, a pressure wave, and a video plethysmogram (VPG) signal.

The second signal may include a ballistocardiogram (BCG) signal.

The processor may obtain one or more candidate characteristic points from the second signal; calculate one or more time intervals between each of the one or more candidate characteristic points and the first characteristic point; and obtain the second characteristic point based on the one or more time intervals of each of the one or more candidate characteristic points and the pre-defined probability distribution function.

The processor may obtain, as the second characteristic point, a candidate characteristic point having a maximum likelihood among the one or more time intervals of each of the one or more candidate characteristic points by using the pre-defined probability distribution function.

By using the pre-defined probability distribution function, the processor may determine the one or more candidate characteristic points having a likelihood, which is greater than or equal to a predetermined threshold value, among the one or more time intervals of each of the one or more candidate characteristic points; and obtain a candidate characteristic point, which satisfies a predetermined condition, as the second characteristic point from among the one or more candidate characteristic points having the likelihood that is greater than or equal to the predetermined threshold value.

The predetermined condition may include at least one of a first condition that an amplitude of the one or more candidate characteristic points is within a predetermined range, and a second condition that a negative peak value exists within a predetermined time interval before and after the one or more candidate characteristic points.

The processor may determine a detection region of the second signal based on the first characteristic point of the first signal; and obtain the second characteristic point in the detection region.

The pre-defined probability distribution function is pre-defined based on distribution of time intervals between first characteristic points of first signals and candidate characteristic points of second signals, which are acquired from a plurality of users.

In response to a personalization condition of the pre-defined probability distribution function being satisfied, the processor may generate a personalized probability distribution function which is personalized for the user based on a plurality of first signals and second signals acquired from the user.

The personalization condition of the pre-defined probability distribution function may be a condition that a number of beats of the second signal, acquired from the user, is greater than or equal to a predetermined threshold value.

The processor may obtain features related to the bio-information of the user based on the second characteristic point; and obtain the bio-information of the user based on the features related to the bio-information of the user.

The bio-information may include at least one of blood pressure, vascular age, arterial stiffness, aortic pressure waveform, stress index, and fatigue level.

According to an aspect of the disclosure, a method of estimating bio-information of a user may include measuring a first signal from the user; measuring a second signal from the user; obtaining a first characteristic point from the first signal; obtaining a second characteristic point from the second signal based on the obtained first characteristic point and a pre-defined probability distribution function; and estimating the bio-information of the user based on the second characteristic point.

The obtaining the second characteristic point may include obtaining one or more candidate characteristic points from the second signal; calculating one or more time intervals between each of the one or more candidate characteristic points and the first characteristic point; and obtaining the second characteristic point based on the one or more time intervals of each of the one or more candidate characteristic points and the pre-defined probability distribution function.

The obtaining the second characteristic point may include obtaining, as the second characteristic point, a candidate characteristic point having a maximum likelihood among the one or more time intervals of each of the one or more candidate characteristic points by using the pre-defined probability distribution function.

The obtaining the second characteristic point may include determining a detection region of the second signal based on the first characteristic point of the first signal; and obtaining the second characteristic point in the detection region.

The method may include determining whether a personalization condition of the pre-defined probability distribution function is satisfied; and generating a personalized probability distribution function, which is personalized for the user, based on a plurality of first signals and second signals acquired from the user.

The method may include obtaining features related to the bio-information of the user based on the second characteristic point; and obtaining the bio-information of the user based on the features related to bio-information of the user.

According to an aspect of the disclosure, an apparatus for estimating bio-information of a user may include a communication interface configured to receive a first signal, measured from the user, from an external device; a second sensor configured to measure a second signal from the user; and a processor configured to obtain a first characteristic point from the first signal; obtain a second characteristic point from the second signal based on the first characteristic point and a pre-defined probability distribution function; and estimate the bio-information of the user based on the second characteristic point.

BRIEF DESCRIPTION OF THE DRAWINGS

The above and other aspects, features, and advantages of certain embodiments of the present disclosure will be more apparent from the following description taken in conjunction with the accompanying drawings, in which.

Figure 1:
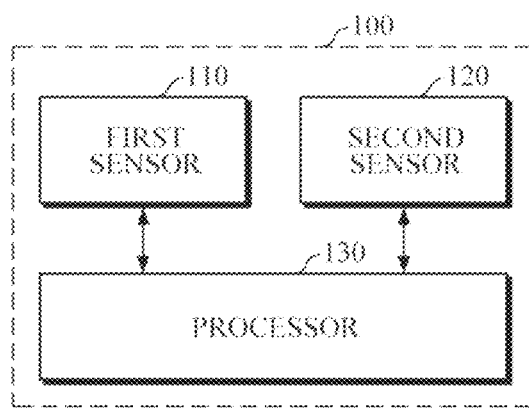
FIGS. 1 to 3 are block diagrams illustrating an apparatus for estimating bio-information according to embodiments of the present disclosure.

Throughout the drawings and the detailed description, unless otherwise described, the same drawing reference numerals will be understood to refer to the same elements, features, and structures. The relative size and depiction of these elements, features, and structures may be exaggerated for clarity, illustration, and convenience.

DETAILED DESCRIPTION

Details of example embodiments are included in the following detailed description and drawings. Advantages and features of the present disclosure, and a method of achieving the same will be more clearly understood from the following embodiments described in detail with reference to the accompanying drawings. Throughout the drawings and the detailed description, unless otherwise described, the same drawing reference numerals will be understood to refer to the same elements, features, and structures.

It will be understood that, although the terms "first," "second," etc. may be used herein to describe various elements, these elements should not be limited by these terms. These terms are only used to distinguish one element from another. Any references to the singular form of a term may include the plural form of the term unless expressly stated otherwise. In addition, unless explicitly described to the contrary, an expression such as "comprising" or "including" will be understood to imply the inclusion of stated elements but not the exclusion of any other elements. Also, terms such as "part," "module," etc., should be understood as a unit that performs at least one function or operation and that may be embodied as hardware, software, or a combination thereof.

Hereinafter, embodiments of an apparatus and method for estimating bio-information will be described in detail with reference to the accompanying drawings.

Figure 2:
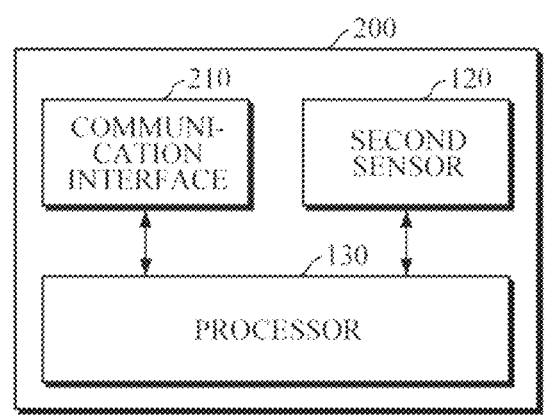
Figure 3:
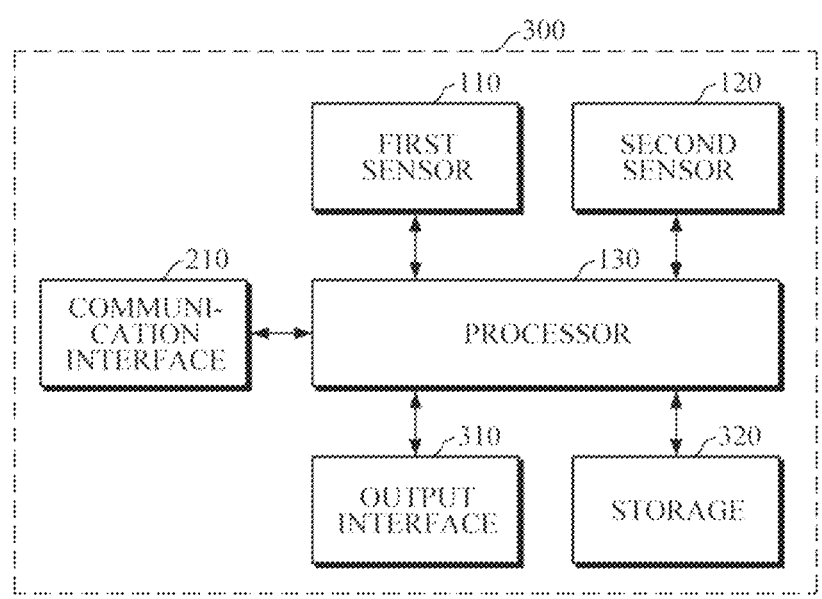

FIGS. 1 to 3 are block diagrams illustrating an apparatus for estimating bio-information according to embodiments of the present disclosure.

Various embodiments of the apparatus for estimating bio-information may be embedded as a software module or a hardware chip in an electronic device. In this case, examples of the electronic device may include a portable device such as a cellular phone, a smartphone, a tablet personal computer (PC), a laptop computer, a personal digital assistant (PDA), a portable multimedia player (PMP), a navigation device, an MP3 player, a digital camera, and the like, or various wearable devices such as a smart watch, a smart band, an earbud, an earphone, and the like, but the electrode device is not limited thereto.

Referring to FIG. 1, the apparatus 100 for estimating bio-information according to an embodiment of the present disclosure includes a first sensor 110, a second sensor 120, and a processor 130.

In the embodiment, the first sensor 110 and the second sensor 120 may be mounted in one electrode device.

The first sensor 110 may acquire a first signal from a user. For example, the first sensor 110 may be a photoplethysmogram (PPG) sensor for measuring a PPG signal. In this case, the PPG sensor may include one or more light sources for emitting light onto a user's object and one or more detectors for detecting light reflected or scattered from the object. In this case, the light source may include a light emitting diode (LED), a laser diode (LD), a phosphor, and the like. The light sources may be one light source or an array of two or more light sources, and each light source may emit light of different wavelengths. Further, the detector may include a photodiode, an image sensor, and the like, and may be one detector or an array of two or more detectors.

However, the first sensor 110 is not limited to the PPG sensor, and may include a sensor for measuring an electrocardiography (ECG) signal, an electromyography (EMG)

signal, an impedance plethysmogram (IPG) signal, a pressure wave, a video plethysmogram (VPG) signal, and the like.

The second sensor 120 may acquire a second signal from the user. In this case, the second signal may be a ballistocardiogram (BCG) signal, but is not limited thereto. For example, the second sensor 120 may include various types of sensors for measuring the BCG signal, such as a displacement sensor, a velocity sensor, an acceleration sensor, a load cell sensor, a polyvinylidene fluoride (PVDF) film sensor, an electro mechanical film (EMFi) sensor, a force sensor, and the like.

The processor 130 may be electrically connected to the first sensor 110 and the second sensor 120. The processor 130 may interact with the user and may process the user's various requests. In addition, based on receiving a request for estimating bio-information from the user, the processor 130 may control the first sensor 110 and the second sensor 120.

By using the first signal and the second signal, the processor 130 may obtain characteristic points for estimating bio-information. In this case, the bio-information may include blood pressure, vascular age, arterial stiffness, aortic pressure waveform, stress index, fatigue level, and the like, but is not limited thereto.

For example, the processor 130 may obtain a first characteristic point from the first signal, and may obtain a second characteristic point from the second signal by using the obtained first characteristic point and a probability distribution function. In this case, the probability distribution function may be generated using frequency, with which values of time intervals between the first characteristic point of the first signal and the characteristic points of the second signal appear. The probability distribution function may be a universal probability distribution function which is pre-generated based on first signals and second signals acquired from a plurality of users, or may be a personalized probability distribution function which is generated based on a plurality of first signals and second signals acquired from a specific user.

Based on obtaining the second characteristic point from the second signal, the processor 130 may obtain features related to bio-information based on the second characteristic point, and may estimate bio-information by using the obtained features.

Referring to FIG. 2, an apparatus 200 for estimating bio-information according to an embodiment of the present disclosure includes a communication interface 210 in addition to the second sensor 120 and the processor 130.

In the embodiment, without the first sensor for measuring the first signal, the apparatus 200 for estimating bio-information may measure the first signal by using an external device for measuring the first signal through the communication interface 210.

For example, based on receiving a request for estimating bio-information from a user, the processor 130 may control an external device through the communication interface 210 simultaneously with controlling the second sensor 120. In this case, the external device may be a smartphone having the first sensor, a wearable device, and the like. The processor 130 may control the external device to measure the first signal from a first object of the user, and at the same time may control the second sensor 120 to measure the second signal from a second object. For example, the first object may be the user's finger and the second object may be the user's wrist. That is, in the case where the apparatus 200 for estimating bio-information is mounted in a smart watch worn on the wrist and the external device is a smartphone, and when the user touches the first sensor of the smartphone with the finger while wearing the smart watch on the wrist, the first signal and the second signal may be measured at the same time. However, the measurement is not limited thereto.

The communication interface 210 may communicate with the external device by using wired and wireless communication techniques under the control of the processor 130, and may receive and transmit a control signal of the processor 130 and/or the first signal measured by the external device. In this case, examples of the wired and wireless communication techniques include Bluetooth communication, Bluetooth Low Energy (BLE) communication, Near Field Communication (NFC), wireless local area network (WLAN) communication, Zigbee communication, Infrared Data Association (IrDA) communication, wireless fidelity (Wi-Fi) Direct (WFD) communication, Ultra-Wideband (UWB) communication, Ant+ communication, Wi-Fi communication, Radio Frequency Identification (RFID) communication, 3G communication, 4G communication, 5G communication, and the like. However, the communication techniques are not limited thereto.

Based on the first signal and the second signal being acquired, the processor 130 may obtain the first characteristic point from the first signal and may obtain the second characteristic point for estimating bio-information from the second signal by using the probability distribution function, as described above. Further, the processor 130 may estimate bio-information based on the obtained second characteristic point.

Referring to FIG. 3, an apparatus 300 for estimating bio-information according to an embodiment of the present disclosure includes the first sensor 110, the second sensor 120, the processor 130, the communication interface 210, an output interface 310, and a storage 320. In this case, the first sensor 110 may be omitted as described in FIG. 2.

As described above, the communication interface 210 may receive the first signal from an external device under the control of the processor 130. In addition, the communication interface 210 may receive, from the external device, a variety of information for estimating bio-information such as, for example, reference information such as a pre-defined universal probability distribution function, a bio-information estimation model, and the like. Further, based on the processor 130 obtaining a bio-information estimation result, the communication interface 210 may transmit the bio-information estimation result to the external device.

The output interface 310 may output processing results of the processor 130. For example, the output interface 310 may provide a user with information such as characteristic points obtained from each of the first signal and the second signal, the bio-information estimation result, health condition information based on the bio-information estimation result, warning information, and the like, by using various output modules. For example, the output interface 310 may provide the information by various visual/non-visual methods using a display module, a speaker, a haptic module, and the like.

The storage 320 may store programs or commands for processing various operations performed by the apparatus 300 for estimating bio-information. Further, the storage 320 may store a variety of reference information for estimating bio-information and various data generated by the first sensor 110, the second sensor 120 and the processor 130. In this case, the reference information may include various types of information used for estimating bio-information, such as the pre-defined probability distribution function, the bio-information estimation model, a user's age, sex, health condition, and the like.

In this case, the storage 320 may include least one storage medium of a flash memory type memory, a hard disk type memory, a multimedia card micro type memory, a card type memory (e.g., a secure digital (SD) memory, an extreme digital (XD) memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, and the like. Further, the storage 320 may include an external storage medium such as web storage, and the like.

Figure 4:
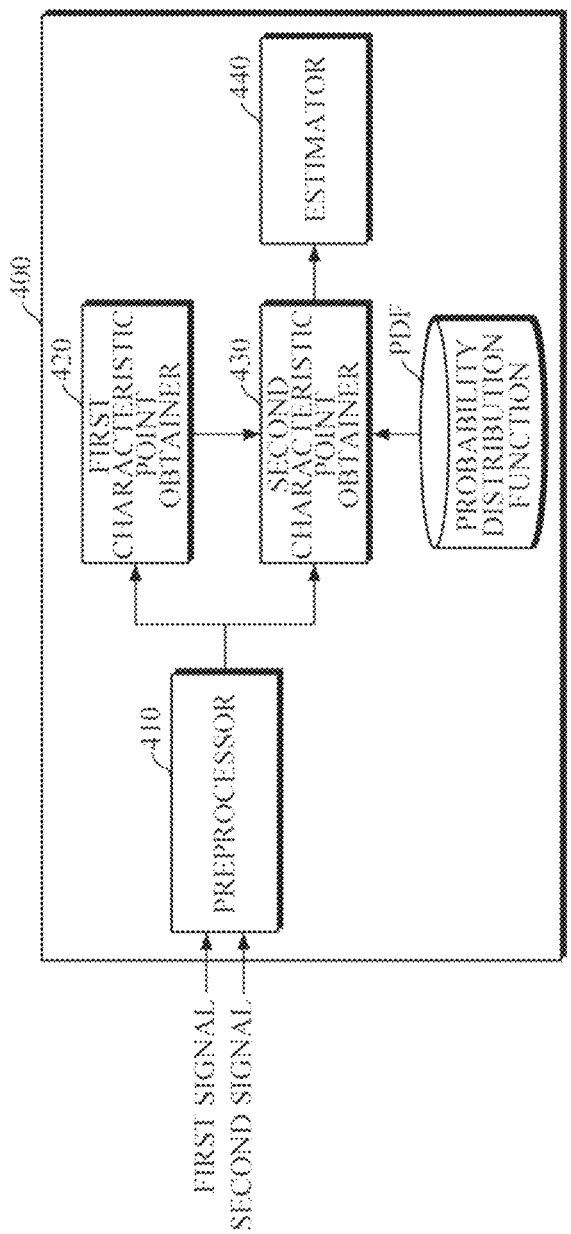
FIGS. 4 and 5 are block diagrams illustrating embodiments of a processor of FIGS. 1 to 3.
Figure 5:
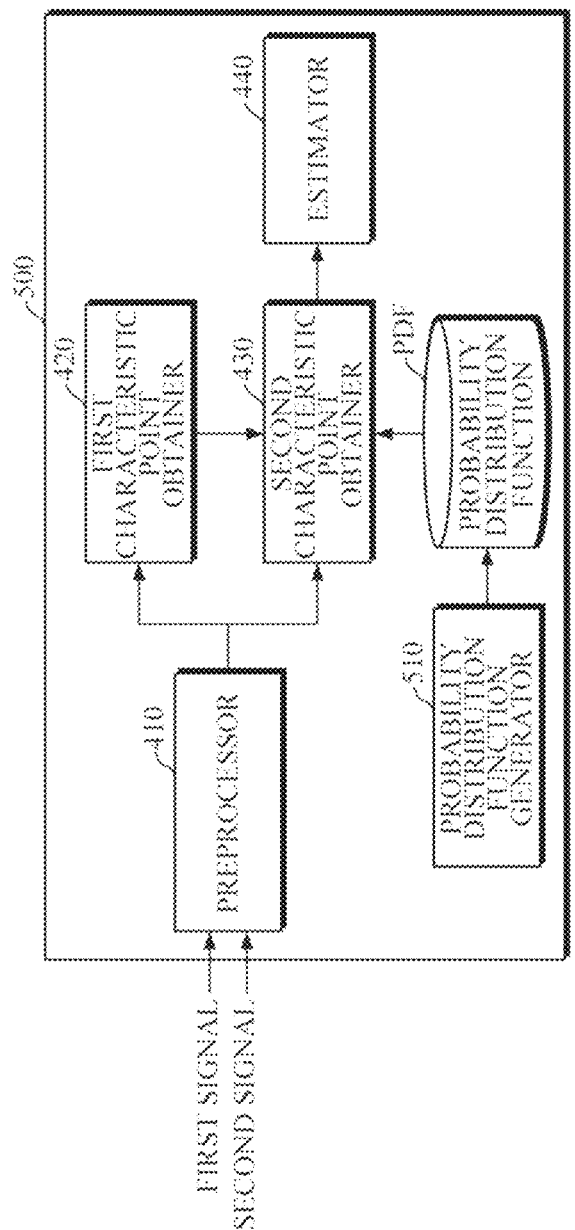

FIGS. 4 and 5 are block diagrams illustrating embodiments of a processor 130 of FIGS. 1 to 3. FIGS. 6A to 6D are diagrams explaining examples of obtaining characteristic points from a BCG signal.

Referring to FIG. 4, the processor 130 according to an embodiment of the present disclosure includes a preprocessor 410, a first characteristic point obtainer 420, a second characteristic point obtainer 430, and an estimator 440.

The preprocessor 410 may preprocess a first signal and a second signal. For example, based on receiving the first signal and the second signal, the preprocessor 410 may remove noise, such as motion noise, by using various noise removal methods such as filtering, smoothing, and the like. For example, if the first signal is an ECG signal, the preprocessor 410 may perform band-pass filtering with a cutoff frequency of 1 Hz to 40 Hz; if the first signal is a PPG signal, the preprocessor 410 may perform band-pass filtering with a cutoff frequency of 1 Hz to 10 Hz; and if the second signal is a BCG signal, the preprocessor 410 may perform band-pass filtering with a cutoff frequency of 0.8 Hz to 20 Hz.

Figure 6A:
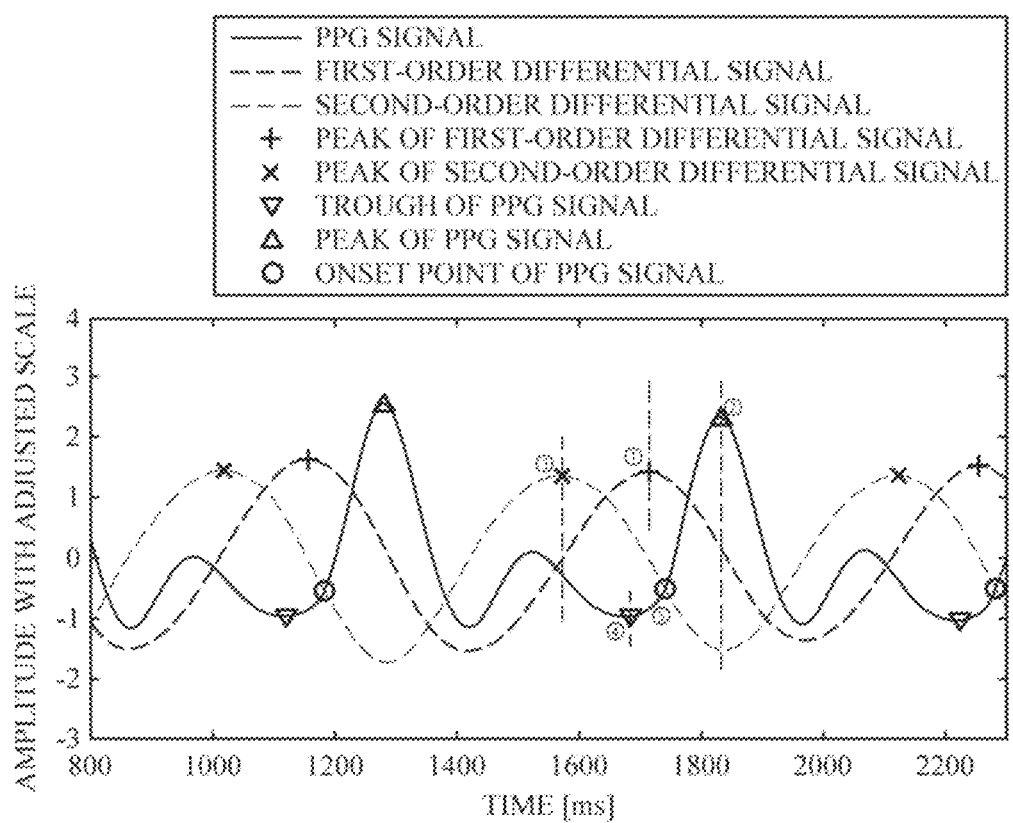
FIGS. 6A to 6D are diagrams explaining examples of obtaining characteristic points from a BCG signal.

The first characteristic point obtainer 420 may obtain a first characteristic point, which is used as a reference for obtaining a second characteristic point of the second signal, from the first signal. For example, FIG. 6A illustrates a PPG signal as the first signal, and various characteristic points which can be detected from the PPG signal. As illustrated in FIG. 6A, various characteristic points which can be detected from the PPG signal may include, for example, a local maximum point ① of a first-order differential signal, a local maximum point ② of the PPG signal in an interval after the local maximum point of the first-order differential signal, a local maximum point ③ of a second-order differential signal, a local minimum point ④ of the PPG signal in an interval between the local maximum point ② of the PPG signal and the local maximum point ③ of the second-order differential signal, an onset point ⑤ of the PPG signal using the local maximum point ② of the PPG signal and the local minimum point ④ of the PPG signal, and the like, but is not limited thereto.

As described above, the first characteristic point obtainer 420 may determine, as the first characteristic point used as reference for obtaining the second characteristic point, any one predetermined characteristic point, e.g., the onset point ⑤ of the PPG signal among various characteristic points which may be detected from the first signal. In this case, the first characteristic point is not limited to the onset point of the PPG signal, and may be defined differently according to various criteria such as a type of the first signal, a type of the second signal, a user's age, sex, health condition, and the like. For example, if the first signal is the PPG signal, the first characteristic point obtainer 420 may determine the local maximum point of the PPG signal as the first characteristic point in addition to the onset point of the PPG signal, and if the first signal is the ECG signal, the first characteristic point obtainer 420 may determine the R-wave as the first characteristic point.

The second characteristic point obtainer 430 may obtain a one-period signal by segmenting the second signal by performing beat gating on the second signal based on the first characteristic point obtained by the first characteristic point obtainer 420. Further, the second characteristic point obtainer 430 may determine a detection region from the one-period signal of the obtained second signal based on the first characteristic point, and may obtain the second characteristic point in the determined detection region.

Hereinafter, an example of obtaining the second characteristic point from the second signal will be described with reference to FIGS. 6B and 6C. In this case, FIG. 6B illustrates a case in which the first signal is the PPG signal and the second signal is the BCG signal, and FIG. 6C illustrates a case where the first signal is the ECG signal and the second signal is the BCG signal.

Figure 6B:
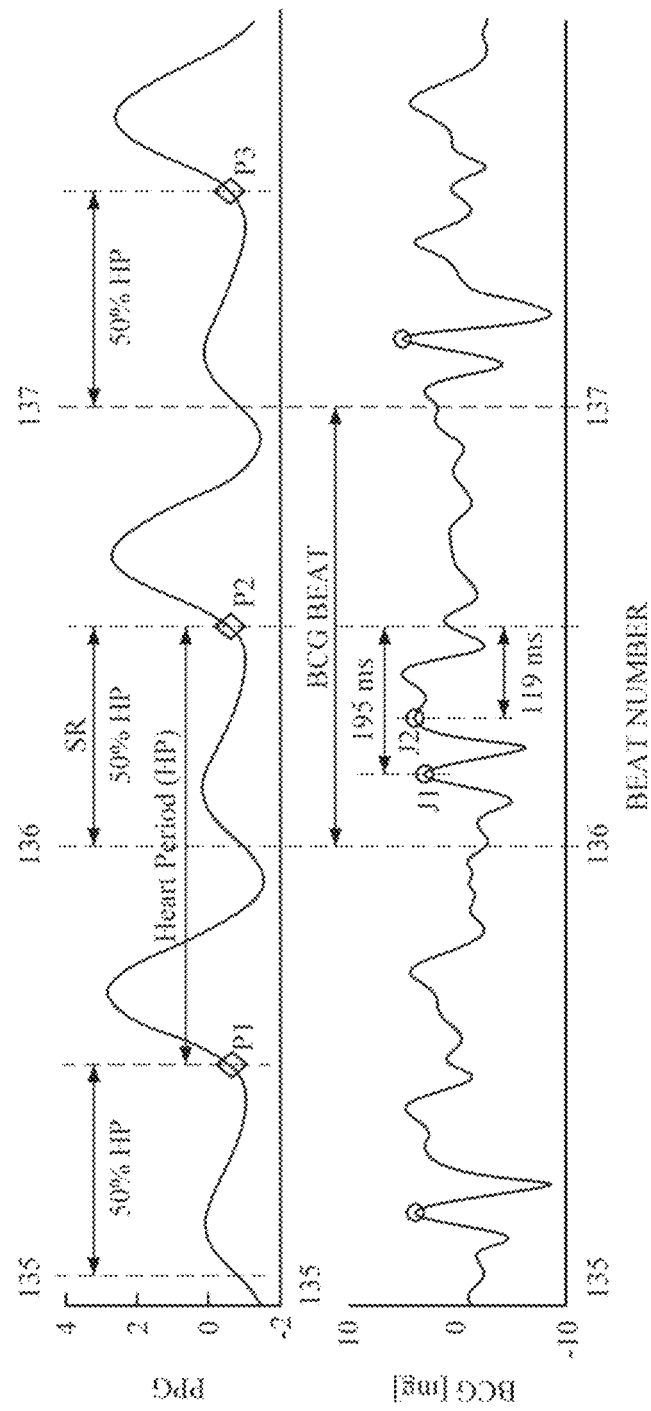
Figure 6C:
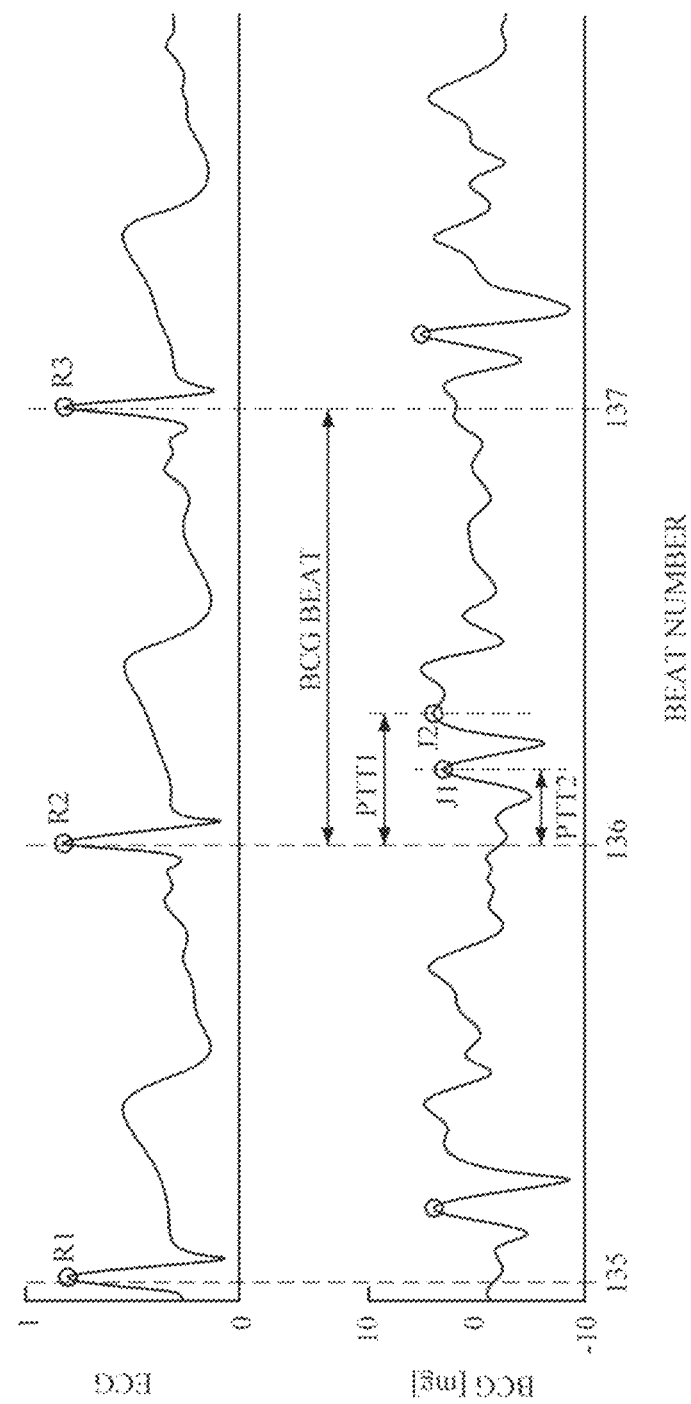

Referring to FIG. 6B, the first characteristic point obtainer 420 may obtain onset points P1, P2 and P3 as the first characteristic points from the PPG signal. The second characteristic point obtainer 430 may segment the signal into one-period signals (e.g., beat numbers 135, 136 and 137) by gating the BCG signal based on points corresponding to 50% of a heart period (HP) of the first characteristic points P1, P2 and P3. The second characteristic point obtainer 430 may select, as a representative signal, a one-period signal (e.g., beat number 136) from among the segmented one-period signals, and may obtain a BCG characteristic point in the selected representative signal (e.g., beat number 136) as the second characteristic point for use in estimating bio-information.

For example, the second characteristic point obtainer 430 may set an interval, corresponding to the 50% heart period (HP) preceding the first characteristic point P2, as a detection region SR in the representative signal, and may obtain J-wave points J1 and J2 of the BCG signal as candidate characteristic points in the detection region. In this case, depending on a type of the first signal, the second characteristic point obtainer 430 may determine different intervals of the BCG signal as the detection region.

Based on detecting the candidate characteristic points J1 and J2 in the BGC signal, the second characteristic point obtainer 430 may determine at least one of the candidate characteristic points J1 and J2 as the second characteristic point by using the first characteristic point P2 and a pre-defined probability distribution function (PDF). In this case, the probability distribution function is a universal probability distribution function (PDF), i.e., a PDF which is pre-defined by obtaining time intervals between the first characteristic point of the first signal and the candidate characteristic points of the second signal, which are obtained for a plurality of users, and by using frequency of the obtained time intervals.

Figure 6D:
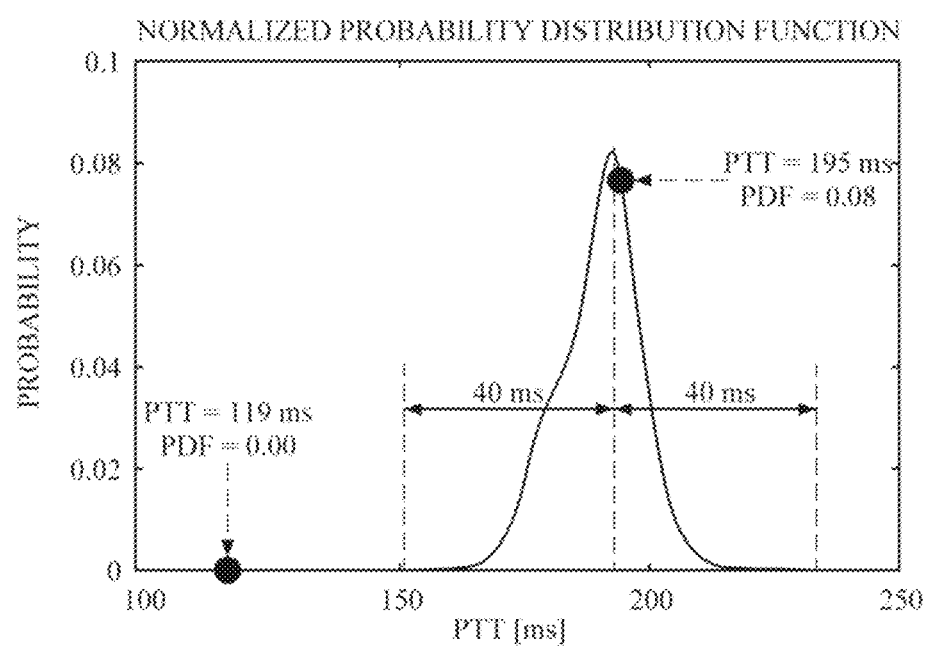

For example, the second characteristic point obtainer 430 may calculate time intervals between the first characteristic point P2 and the candidate characteristic points J1 and J2 of the BCG signal, and may determine a candidate characteristic point, having a maximum likelihood in the probability distribution function (PDF), as the second characteristic point among the calculated time intervals of the candidate characteristic points. For example, as illustrated in FIG. 6B, a time interval between the first characteristic point P2 and the candidate characteristic point J1 of the BCG signal is 195 ms, and a time interval between the first characteristic point P2 and the candidate characteristic point J2 of the BCG signal is 119 ms. FIG. 6D illustrates a normalized probability distribution function (PDF), in which a probability for a time interval (195 ms) of the candidate characteristic point J1 is 0.08 and a probability for a time interval (119 ms) of the candidate characteristic point J2 is 0.00, such that the candidate characteristic point J1 may be determined as the second characteristic point.

In another example, the second characteristic point obtainer 430 may determine candidate characteristic points, having a likelihood in the probability distribution function (PDF) which is greater than or equal to a predetermined threshold value, among time intervals calculated for all the candidate characteristic points J1 and J2 of the BCG signal, and may determine a candidate characteristic point, which satisfies a predetermined condition, as the second characteristic point among the determined candidate characteristic points. For example, if the second signal is the BCG signal, the second characteristic point obtainer 430 may determine a candidate characteristic point, which has a highest likelihood and satisfies a first condition that an amplitude is within a predetermined range (e.g., 2 mg to 20 mg) and a second condition that a negative peak value exists within 100 ms before/after the candidate characteristic point, as the second characteristic point among candidate characteristic points having a likelihood greater than or equal to a predetermined threshold value for each time interval of the PDF.

Referring to FIG. 6C, the first characteristic point obtainer 420 may obtain R-waves R1, R2 and R3 of the ECG signal as the first characteristic points. By performing gating on the signal based on the R-waves, the second characteristic point obtainer 430 may segment the ECG signal into one-period signals (e.g., beat numbers 135, 136, and 137). As described above, the second characteristic point obtainer 430 may obtain the candidate characteristic points J1 and J2 of the BCG signal by using any one one-period signal (beat number 136). In this case, by considering that the first signal is the ECG signal, the second characteristic point obtainer 430 may set an interval of a one-period signal following the first characteristic point R2 as a detection region, and may obtain the candidate characteristic points J1 and J2 in the set detection region. The second characteristic point obtainer 430 may determine the second characteristic point by the aforementioned various methods using the PDF and the time intervals PTT2 and PTT1 between the obtained candidate characteristic points J1 and J2 and the first characteristic point R2.

As described above, by detecting the characteristic points of the BCG signal by using a pre-defined probability distribution function (PDF), the characteristic points may be detected with a small amount of calculations, and erroneous detection of characteristic points due to noise and the like may be reduced, thereby improving accuracy in estimating bio-information.

The estimator 440 may estimate bio-information by using the second characteristic point obtained by the second characteristic point obtainer 430. For example, the estimator 440 may obtain features, related to bio-information, by using the second characteristic point, and may estimate bio-information by using the obtained features related to bio-information.

For example, the estimator 440 may obtain, as features related to bio-information, time and/or amplitude values of the obtained second characteristic point or a combination thereof, and may estimate bio-information by using a bio-information estimation model which defines a correlation between the time and/or amplitude values of the second characteristic point and a bio-information value. In this case, the bio-information estimation model may be pre-defined using various methods such as linear/nonlinear regression analysis, neural networks, deep learning, and the like.

In another example, if the second characteristic point is a BCG J-peak measured on the wrist, the estimator 440 may obtain a J-K time interval, a K amplitude, a K-L amplitude, and the like as features related to, for example, arterial stiffness, pulse transit time, aortic PP, or Distal PP. In this case, the K-wave of the BCG signal is generally a footward wave occurring after the J-wave, and the L-wave is headward deflection occurring after the K-wave. In this case, blood pressure-related features may be defined differently depending on measurement portions of the BCG signal. The estimator 440 may estimate blood pressure by applying a blood pressure estimation model to the obtained blood pressure-related features.

Referring to FIG. 5, a processor 500 according to an embodiment of the present disclosure includes the preprocessor 410, the first characteristic point obtainer 420, the second characteristic point obtainer 430, the estimator 440, and a probability distribution function generator 510. The preprocessor 410, the first characteristic point obtainer 420, the second characteristic point obtainer 430, and the estimator 440 are described above with reference to FIG. 4, and thus descriptions thereof will be omitted below.

The probability distribution function generator 510 may determine a personalization condition of the probability distribution function, and based on determining that the personalization condition is satisfied, the probability distribution function generator 510 may generate a probability distribution function personalized for a specific user. For example, the personalization condition may be pre-defined, such as a case where the number of beats segmented by beat gating of the second signal is accumulated to be greater than or equal to a predetermined threshold value (e.g., 30), or a case where the number of times of estimating bio-information is greater than or equal to a predetermined threshold value.

For example, at predetermined times, such as based on receiving a user's request for estimating bio-information, based on the first sensor and the second sensor acquiring the first signal and the second signal respectively, or based on the estimator 440 completing estimation of bio-information, the probability distribution function generator 510 may determine whether the personalization condition is satisfied. Based on determining that the personalization condition is satisfied, the probability distribution function generator 510 may generate a personalized probability distribution function by using a plurality of first signals and second signals which are acquired for a specific user. For example, the probability distribution function generator 510 may obtain first characteristic points from each of the plurality of first signals, may obtain candidate characteristic points from each of the plurality of second signals, may calculate time intervals between the first characteristic points and the candidate characteristic points at corresponding times, may generate a personalized probability distribution function by using frequency of the calculated time intervals, and may update a pre-stored probability distribution function (PDF).

If the probability distribution function generator 510 determines that the personalization condition is not satisfied, the second characteristic point may be obtained by using a universal probability distribution function which is pre-defined for a plurality of users, as described above.

Based on generating the probability distribution function personalized for a specific user, the probability distribution function generator 510 may calibrate the probability distribution function at predetermined intervals or in response to a user's request.

Figure 7:
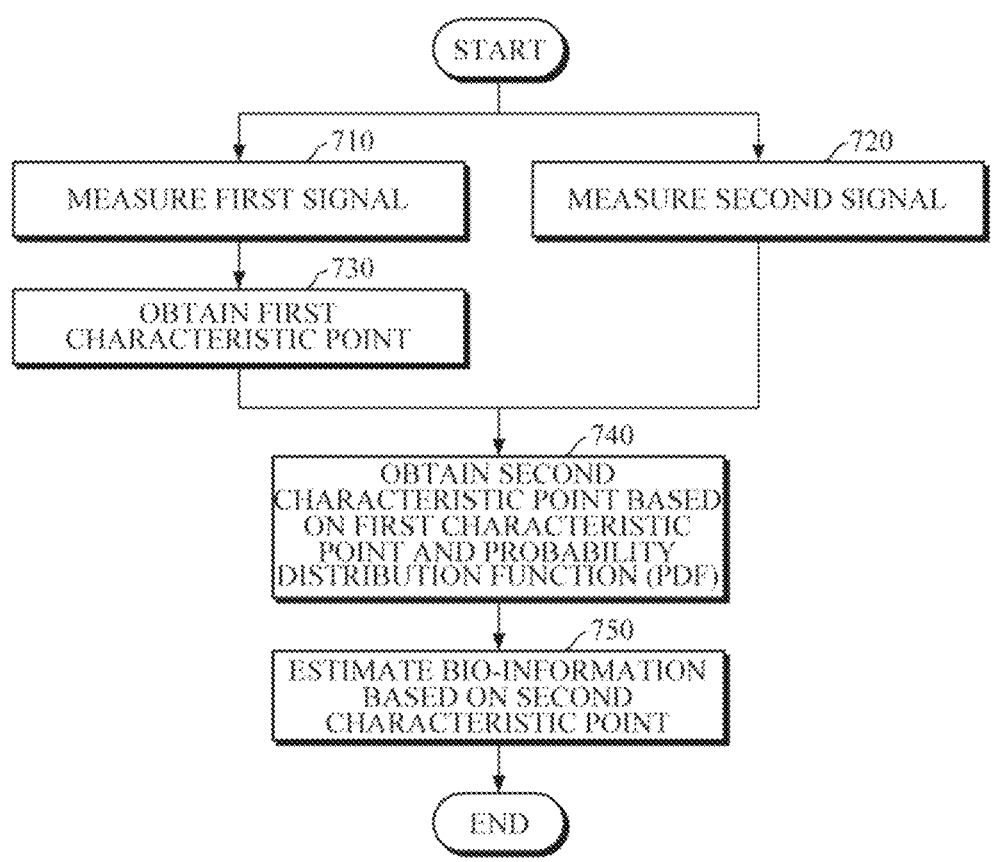
FIG. 7 is a flowchart illustrating a method of estimating bio-information according to an embodiment of the present disclosure.

FIG. 7 is a flowchart illustrating a method of estimating bio-information according to an embodiment of the present disclosure. The method of FIG. 7 may be performed by the apparatuses 100, 200 and 300 for estimating bio-information according to the embodiments of FIGS. 1 to 3, which is described in detail above, and thus will be briefly described below.

In response to a request for estimating bio-information, the apparatuses 100, 200 and 300 for estimating bio-information may measure a first signal in operation 710 and may measure a second signal in operation 720. The first signal may include an ECG signal, a PPG signal and the like, and the second signal may include a BCG signal. The first signal and the second signal may be measured concurrently, substantially concurrently, at different times, etc.

Then, the apparatuses 100, 200 and 300 for estimating bio-information may obtain a first characteristic point from the first signal in operation 730. For example, in the case of the PPG signal, the first characteristic point may be a PPG onset point; and in the case of the ECG signal, the first characteristic point may be an R-wave, but the first characteristic point is not limited thereto.

Subsequently, the apparatuses 100, 200 and 300 for estimating bio-information may obtain a second characteristic point from the second signal based on the first characteristic point and a probability distribution function (PDF) in operation 740. For example, the apparatuses 100, 200 and 300 for estimating bio-information may obtain a representative one-period signal by performing beat gating on the second signal based on the first characteristic point, and may obtain the second characteristic point from the obtained representative signal. For example, if the second signal is the BCG signal, the apparatuses 100, 200 and 300 for estimating bio-information may obtain J-peaks as candidate characteristic points in a time interval of the representative signal preceding the first characteristic point, may calculate time intervals between the first characteristic point and each of the candidate characteristic points, and may obtain, as the second characteristic point, a candidate characteristic point having a maximum likelihood in the PDF or a candidate characteristic point satisfying a predetermined condition, which is described above in detail, and thus a description thereof will be omitted below.

Next, the apparatuses 100, 200 and 300 for estimating bio-information may estimate bio-information based on the second characteristic point in operation 750. For example, the apparatuses 100, 200 and 300 for estimating bio-information may obtain features related to bio-information based on the second characteristic point, and may estimate bio-information by using a pre-defined bio-information estimation model based on the features related to bio-information. Further, the apparatuses 100, 200 and 300 for estimating bio-information may output an estimated bio-information value, warning information based on the estimated bio-information value, and the like.

Figure 8:
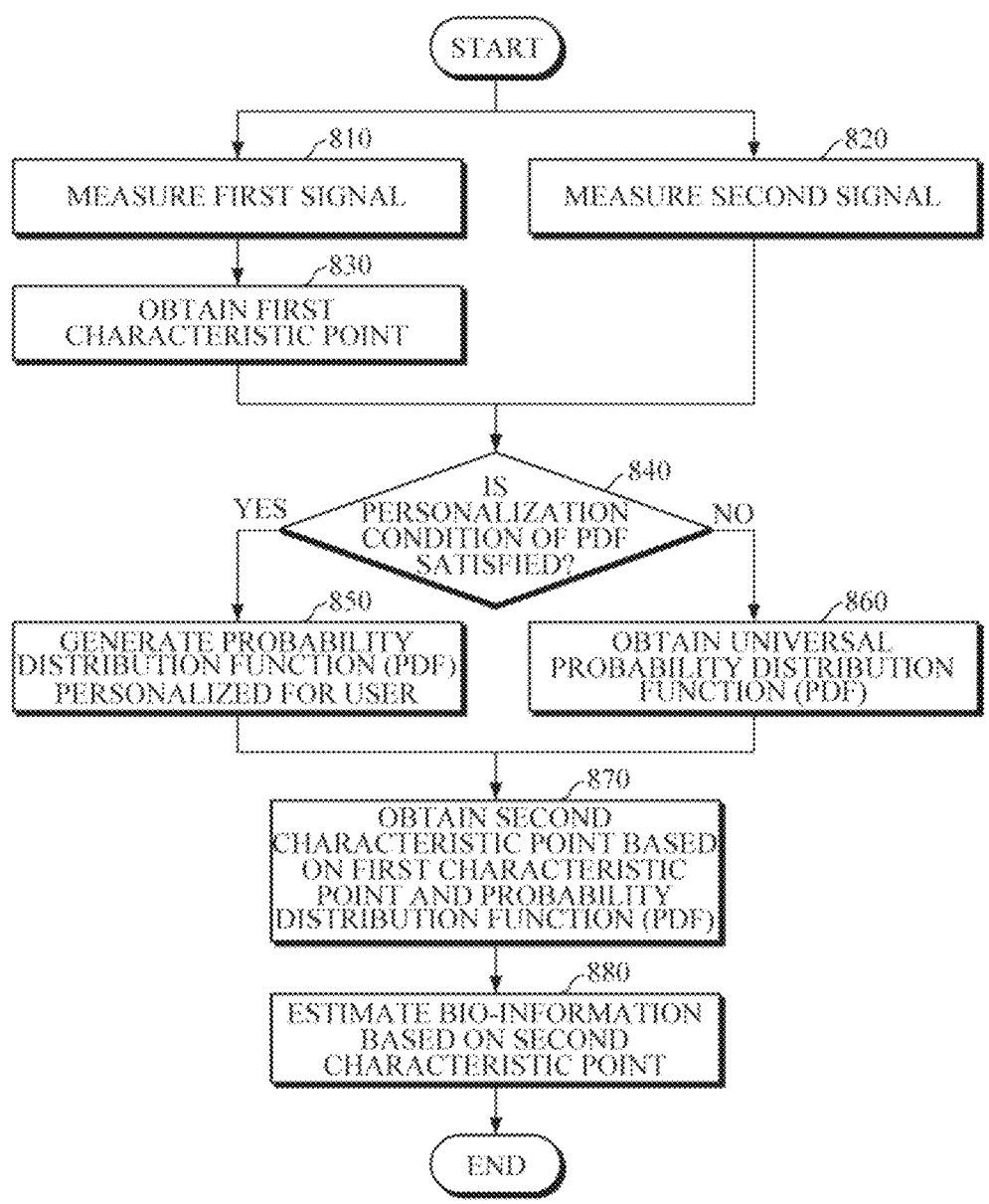
FIG. 8 is a flowchart illustrating a method of estimating bio-information according to another embodiment of the present disclosure.

FIG. 8 is a flowchart illustrating a method of estimating bio-information according to another embodiment of the present disclosure. The method of FIG. 8 may be performed by the apparatuses 100, 200 and 300 for estimating bio-information according to the embodiments of FIGS. 1 to 3, which is described in detail above, and thus will be briefly described below.

In response to a request for estimating bio-information, the apparatuses 100, 200 and 300 for estimating bio-information may measure a first signal in operation 810 and may measure a second signal in operation 820.

Then, the apparatuses 100, 200 and 300 for estimating bio-information may obtain a first characteristic point from the first signal in operation 830.

Subsequently, the apparatuses 100, 200 and 300 for estimating bio-information may determine whether a personalization condition of a probability distribution function (PDF) is satisfied in operation 840. In this case, the personalization condition may be defined such that the PDF is personalized if a number of beats of the second signal, which is acquired for a specific user, is greater than or equal to a predetermined threshold value, or if a cumulative number of times of estimating bio-information is greater than or equal to a predetermined threshold value. However, the personalization condition is not limited thereto. In this case, the determining of the personalization condition in operation 840 is not necessarily performed after the obtaining of the first characteristic point in 830, and in response to receipt of a request for estimating bio-information, the determining of the personalization condition in 840 may be performed before the measuring of the first signal in 810 or after estimating of bio-information in 880.

Then, based on determining in operation 840 that the personalization condition is satisfied, the apparatuses 100, 200 and 300 for estimating bio-information may generate a probability distribution function, which is personalized for a specific user, by using a plurality of first signals and second signals acquired from the specific user in 850. A detailed description thereof will be omitted.

Based on determining in 840 that the personalization condition is not satisfied, the apparatuses 100, 200 and 300 for estimating bio-information may obtain a universal probability distribution function in operation 860, which is pre-defined for a plurality of users, from a storage or an external device in which the probability distribution function is pre-stored.

Then, the apparatuses 100, 200 and 300 for estimating bio-information may obtain a second characteristic point from the second signals based on the first characteristic point and the probability distribution function in operation 870. A detailed description thereof will be omitted.

Subsequently, the apparatuses 100, 200 and 300 for estimating bio-information may estimate bio-information based on the second characteristic point in operation 880. For example, the apparatuses 100, 200 and 300 for estimating bio-information may obtain features related to bio-information based on the second characteristic point, and may estimate bio-information based on the features related to bio-information by using a pre-defined bio-information estimation model. Further, the apparatuses 100, 200 and 300 for estimating bio-information may output an estimated bio-information value, warning information based on the estimated bio-information value, and the like.

Figure 9:
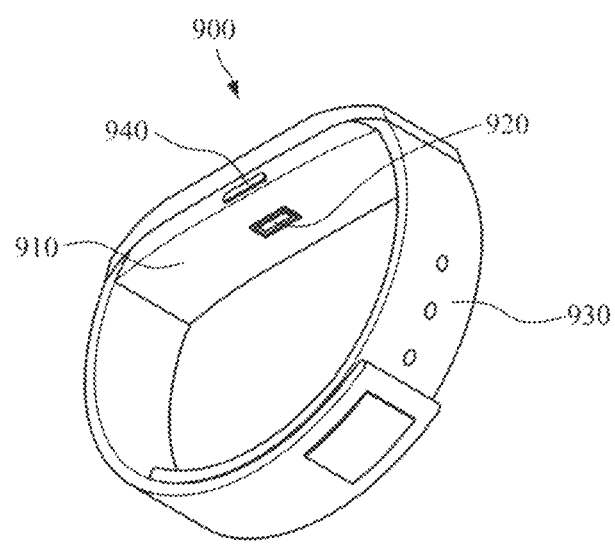
FIG. 9 is a diagram illustrating a wearable device according to an embodiment of the present disclosure.

FIG. 9 is a diagram illustrating a wearable device according to an embodiment of the present disclosure. The aforementioned embodiments of the apparatuses 100, 200 and 300 for estimating bio-information may be mounted in a smart watch worn on a wrist as illustrated in FIG. 9.

Referring to FIG. 9, the wearable device 900 includes a main body 910 and a strap 930.

The main body 910 may be formed to have various shapes, and may include modules which are mounted inside or outside of the main body 910 to perform the aforementioned function of estimating bio-information and various other functions. A battery may be embedded in the main body 910 or the strap 930 to supply power to various modules of the wearable device 900.

The strap 930 may be connected to the main body 910. The strap 930 may be flexible so as to be bent around a user's wrist. The strap 930 may be bent in a manner that allows the strap 930 to be detached from the user's wrist or may be formed as a band that is not detachable. Air may be injected into the strap 930 or an airbag may be included in the strap 930, so that the strap 930 may have elasticity according to a change in pressure applied to the wrist, and the strap 930 may transmit the change in pressure of the wrist to the main body 910.

The main body 910 may include a sensor 920. The sensor 920 may be mounted on a rear surface of the main body 910, which comes into contact with the upper portion of a user's wrist, and may include a PPG sensor which measures a PPG signal from an object and includes a light source for emitting light onto the skin of the wrist and a detector for detecting light scattered or reflected from the object. The sensor 920 may further include an acceleration sensor or a force sensor which measures a BCG signal from the object.

A processor may be mounted in the main body 910, and may be electrically connected to various modules, mounted in the wearable device 900, to control operations thereof. The processor may obtain a reference characteristic point by using a PPG signal measured by the sensor 920, and may obtain a BCG characteristic point from a BCG signal by using the reference characteristic point and a universal probability distribution function or a personalized probability distribution function. Further, the processor may estimate bio-information, e.g., blood pressure, by using the obtained BCG characteristic point.

Further, the main body 910 may include a storage which stores processing results of the processor and a variety of information. In this case, the variety of information may include reference information related to estimating bio-information, as well as information associated with functions of the wearable device 900.

In addition, the main body 910 may also include a manipulator 940 which receives a user's control command and transmits the received control command to the processor. The manipulator 940 may include a power button to input a command to turn on/off the wearable device 900.

A display may be mounted on a front surface of the main body 910, and may include a touch panel for receiving a touch input. The display may receive a touch input from a user, may transmit the received touch input to the processor, and may display a processing result of the processor. For example, the display may display an estimated bio-information value and warning/alarm information.

Moreover, a communication interface, provided for communication with an external device such as a user's mobile terminal, may be mounted in the main body 910. The communication interface may transmit a bio-information estimation result to an external device, e.g., a user's smartphone, to display the result to the user. However, the communication interface is not limited thereto, and may transmit and receive a variety of necessary information.

In addition, if the sensor 920 includes only the sensor for measuring the BCG signal, the communication interface may communicate with an external device, e.g., a smartphone, and may control a PPG sensor mounted in the smartphone to receive a PPG signal from the smartphone. In this case, the processor may generate guide information for guiding a contact position or a contact state of a user's finger being in contact with a display of the smartphone, and may transmit the guide information to the smartphone through the communication interface to output the guide information to the display of the smartphone.

Figure 10:
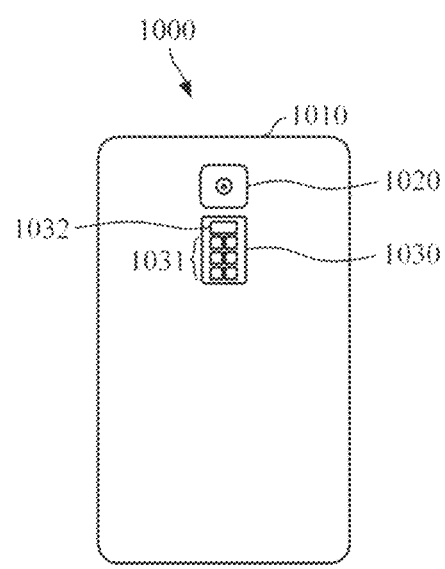
FIG. 10 is a diagram illustrating a smart device according to an embodiment of the present disclosure.

FIG. 10 is a diagram illustrating a smart device according to an embodiment of the present disclosure. In this case, the smart device may be a smartphone, a tablet PC, and the like, and may include the aforementioned apparatuses 100, 200 and 300 for estimating bio-information.

Referring to FIG. 10, the smart device 1000 includes a main body 1010 and a sensor 1030 mounted on one surface of the main body 1010. The sensor 1030 may include a PPG sensor including at least one or more light sources 1031 and a detector 1032. As illustrated in FIG. 10, the sensor 1030 may be mounted on a rear surface of the main body 1010, but is not limited thereto, and may be configured in combination with a fingerprint sensor or a touch panel mounted on a front surface of the main body 1010. In addition, the main body 1010 may further include an acceleration sensor or a force sensor which measures a BCG signal.

Further, a display may be mounted on a front surface of the main body 1010. The display may visually display a bio-information estimation result and the like. The display may include a touch panel, and may receive a variety of information input through the touch panel and transmit the received information to the processor.

Moreover, an image sensor 1020 may be mounted in the main body 1010. When a user's finger approaches the sensor 1030 to measure a PPG signal, the image sensor 1020 may capture an image of the finger and may transmit the captured image to the processor. In this case, based on the image of the finger, the processor may identify a relative position of the finger with respect to an actual position of the sensor 1030, and may provide the relative position of the finger to the user through the display, so as to guide measurement of pulse wave signals with improved accuracy.

As described above, the processor may estimate bio-information based on the PPG signal and the BCG signal measured by the sensor 1030. For example, the processor may obtain a reference characteristic point from the PPG signal, and may estimate bio-information by obtaining a BCG characteristic point from the BCG signal based on the obtained reference characteristic point and the probability distribution function.

Figure 11A:
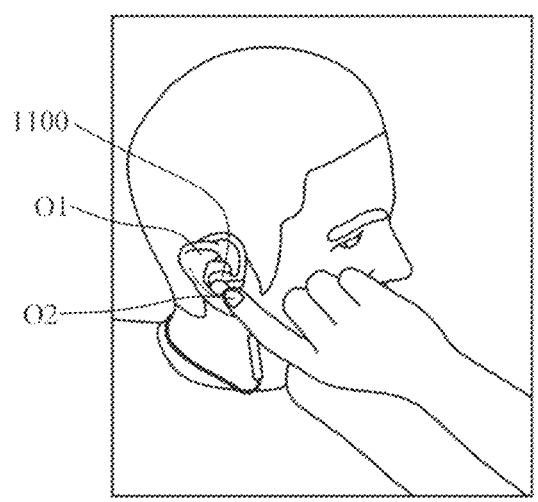
FIGS. 11A to 11C are diagrams illustrating an earphone according to an embodiment of the present disclosure.
Figure 11B:
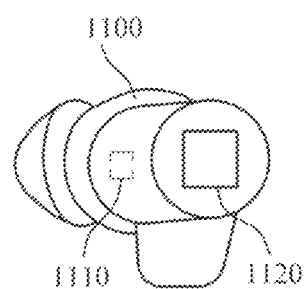
Figure 11C:
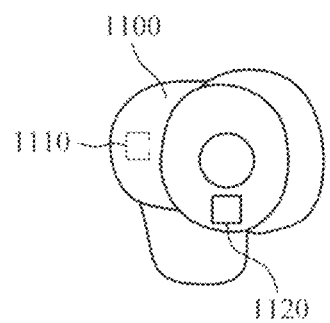

FIGS. 11A to 11C are diagrams illustrating an earphone according to an embodiment of the present disclosure. Various embodiments of the aforementioned apparatuses 100, 200 and 300 for estimating bio-information may be mounted in a device, such as an earphone illustrated in FIGS. 11A to 11C. Here, the earphone includes a wired or wireless earphone, and may be an earbud-type earphone, a necklace-type earphone, an earning-type earphone, and the like, with no limitation on the type of earphones.

Referring to FIGS. 11A and 11B, when a user inserts an earphone 1100 into an ear 01 and touches the earphone 1100 with a finger 02, a PPG signal and a BCG signal may be measured, and bio-information may be estimated by using the measured PPG signal and BCG signal. For example, referring to FIG. 111B, a BCG sensor 1110 for measuring the BCG signal may be mounted in the earphone 1100. Further, a PPG sensor 1120 may be disposed on an outer side of the earphone 1100 to measure the PPG signal from the finger being in contact with the earphone 1100 while the earphone 1100 is inserted into the ear. In this case, the BCG sensor 1110 and the PPG sensor 1120 may be disposed on both the right and left sides of the earphone 1100 or on any one side thereof.

Referring to FIG. 11C, the PPG signal and the BCG signal may be measured at the same time while the user inserts the earphone 1100 into the ear. For example, the BCG sensor 1110 for measuring the BCG signal may be mounted inside the earphone 1100, and the PPG sensor 1120 may be disposed on an inner side of the earphone 1100 to measure the PPG signal inside the ear being in contact with the earphone 1100 while the earphone 1100 is inserted into the ear. In this case, the BCG sensor 1110 and the PPG sensor 1120 may be disposed on both the right and left sides of the earphone 1100 or on any one side thereof.

Further, a processor for performing the function of estimating bio-information may be mounted in the earphone 1100 or in an earphone controller. In this case, when the earphone 1100 is inserted into the ear, the processor controls the BCG sensor and the PPG sensor, and estimates bio-information by using the BCG signal and the PPG signal as described above. The processor may transmit a bio-information estimation result to an external device, e.g., a smartphone or a wearable device, which is connected by wire or wirelessly to the processor.

In addition, instead of being mounted in the earphone 110, the processor for performing the function of estimating bio-information may be mounted in an external device, e.g., a smartphone or a wearable device, which is connected by wire or wirelessly to the earphone 1100. The processor of the external device may receive the BCG signal and the PPG signal from the BCG sensor 1110 and the PPG sensor 1120 of the earphone 1100, and may estimate bio-information by using the received signals.

The processor of the external device or the earphone 1100 may visually output the bio-information estimation result for the user through a display of the external device. Alternatively, when the earphone 1100 is worn on the ear, the processor may output the bio-information estimation result by voice through the earphone 1100 based on completing estimation of bio-information.

The example embodiments of the present disclosure can be implemented by computer-readable code stored on a non-transitory computer-readable medium and executed by a processor. The computer-readable medium may be any type of recording device in which data is stored in a computer-readable manner.

Examples of the computer-readable medium include a ROM, a RAM, a CD-ROM, a magnetic tape, a floppy disc, an optical data storage, and a carrier wave (e.g., data transmission through the Internet). The computer-readable medium can be distributed over a plurality of computer systems connected to a network so that a computer-readable code is written thereto and executed therefrom in a decentralized manner. Functional programs, code, and code segments for implementing the example embodiments of the present disclosure can be deduced by programmers of ordinary skill in the art.

The present disclosure has been described herein with regard to example embodiments. However, it will be obvious to those skilled in the art that various changes and modifications can be made without changing technical ideas of the present disclosure. Thus, it is clear that the above-described embodiments are illustrative in all aspects and are not intended to limit the present disclosure.

What is claimed is:

1. An apparatus for estimating bio-information of a user, the apparatus comprising:
a first sensor configured to measure a first signal from the user;
a second sensor configured to measure a second signal from the user; and
a processor configured to:
obtain a first characteristic point from the first signal;
obtain a second characteristic point from the second signal based on the first characteristic point and a pre-defined probability distribution function; and
estimate the bio-information of the user based on the second characteristic point,
wherein the processor is further configured to:
obtain one or more candidate characteristic points from the second signal;
calculate one or more time intervals between each of the one or more candidate characteristic points and the first characteristic point; and
obtain the second characteristic point based on the one or more time intervals of each of the one or more candidate characteristic points and the pre-defined probability distribution function, and
wherein the first signal comprises at least one of an electrocardiography (ECG) signal, a photoplethysmogram (PPG) signal, an electromyography (EMG) signal, an impedance plethysmogram (IPG) signal, a pressure wave, and a video plethysmogram (VPG) signal.

2. The apparatus of claim 1, wherein the second signal comprises a ballistocardiogram (BCG) signal.

3. The apparatus of claim 1, wherein the processor is further configured to:
obtain, as the second characteristic point, a candidate characteristic point having a maximum likelihood among the one or more time intervals of each of the one or more candidate characteristic points by using the pre-defined probability distribution function.

4. The apparatus of claim 1, wherein by using the pre-defined probability distribution function, the processor is further configured to:
determine the one or more candidate characteristic points having a likelihood, which is greater than or equal to a predetermined threshold value, among the one or more time intervals of each of the one or more candidate characteristic points; and
obtain a candidate characteristic point, which satisfies a predetermined condition, as the second characteristic point from among the one or more candidate characteristic points having the likelihood that is greater than or equal to the predetermined threshold value.

5. The apparatus of claim 4, wherein the predetermined condition comprises at least one of a first condition that an amplitude of the one or more candidate characteristic points is within a predetermined range, and a second condition that a negative peak value exists within a predetermined time interval before and after the one or more candidate characteristic points.

6. The apparatus of claim 1, wherein the processor is further configured to:
determine a detection region of the second signal based on the first characteristic point of the first signal; and
obtain the second characteristic point in the detection region.

7. The apparatus of claim 1, wherein the pre-defined probability distribution function is pre-defined based on distribution of time intervals between first characteristic points of first signals and candidate characteristic points of second signals, which are acquired from a plurality of users.

8. The apparatus of claim 1, wherein in response to a personalization condition of the pre-defined probability distribution function being satisfied, the processor is further configured to generate a personalized probability distribution function which is personalized for the user based on a plurality of first signals and second signals acquired from the user.

9. The apparatus of claim 8, wherein the personalization condition of the pre-defined probability distribution function comprises a condition that a number of beats of the second signal, acquired from the user, is greater than or equal to a predetermined threshold value.

10. The apparatus of claim 1, wherein the processor is further configured to:
   obtain features related to the bio-information of the user based on the second characteristic point; and
   obtain the bio-information of the user based on the features related to the bio-information of the user.

11. The apparatus of claim 10, wherein the bio-information comprises at least one of blood pressure, vascular age, arterial stiffness, aortic pressure waveform, stress index, and fatigue level.

12. A method of estimating bio-information of a user, the method comprising:
   measuring a first signal from the user;
   measuring a second signal from the user;
   obtaining a first characteristic point from the first signal;
   obtaining a second characteristic point from the second signal based on the obtained first characteristic point and a pre-defined probability distribution function; and
   estimating the bio-information of the user based on the second characteristic point,
   wherein the obtaining the second characteristic point comprises:
      obtaining one or more candidate characteristic points from the second signal;
      calculating one or more time intervals between each of the one or more candidate characteristic points and the first characteristic point; and
      obtaining the second characteristic point based on the one or more time intervals of each of the one or more candidate characteristic points and the pre-defined probability distribution function, and
   wherein the first signal comprises at least one of an electrocardiography (ECG) signal, a photoplethysmogram (PPG) signal, an electromyography (EMG) signal, an impedance plethysmogram (IPG) signal, a pressure wave, and a video plethysmogram (VPG) signal.

13. The method of claim 12, wherein the obtaining the second characteristic point comprises obtaining, as the second characteristic point, a candidate characteristic point having a maximum likelihood among the one or more time intervals of each of the one or more candidate characteristic points by using the pre-defined probability distribution function.

14. The method of claim 12, wherein the obtaining the second characteristic point comprises:
   by using the pre-defined probability distribution function, determining the one or more candidate characteristic points having a likelihood, which is greater than or equal to a predetermined threshold value, among the one or more time intervals of each of the one or more candidate characteristic points; and
   obtaining a candidate characteristic point, which satisfies a predetermined condition, as the second characteristic point from among the one or more candidate characteristic points.

15. The method of claim 12, wherein the obtaining the second characteristic point comprises:
   determining a detection region of the second signal based on the first characteristic point of the first signal; and
   obtaining the second characteristic point in the detection region.

16. The method of claim 12, further comprising:
   determining whether a personalization condition of the pre-defined probability distribution function is satisfied; and
   generating a personalized probability distribution function, which is personalized for the user, based on a plurality of first signals and second signals acquired from the user.

17. The method of claim 12, further comprising:
   obtaining features related to the bio-information of the user based on the second characteristic point; and
   obtaining the bio-information of the user based on the features related to bio-information of the user.

* * * * *